United States Patent
Wood, Jr.

(10) Patent No.: US 7,879,023 B2
(45) Date of Patent: *Feb. 1, 2011

(54) SYSTEM FOR PERFUSION MANAGEMENT

(75) Inventor: Lowell L. Wood, Jr., Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 328 days.

This patent is subject to a terminal disclaimer.

(21) Appl. No.: 11/891,334

(22) Filed: Aug. 9, 2007

(65) Prior Publication Data

US 2008/0058713 A1    Mar. 6, 2008

(51) Int. Cl.
*A61M 25/00* (2006.01)
*A61M 37/00* (2006.01)

(52) U.S. Cl. .................... 604/528; 604/93.01; 604/264; 604/288.04; 604/523

(58) Field of Classification Search .............. 604/93.01, 604/164.01, 187, 194–196, 239, 264, 272; 600/101–183; 606/107
See application file for complete search history.

(56) References Cited

U.S. PATENT DOCUMENTS

| | | |
|---|---|---|
| 3,391,697 A | 7/1968 | Greatbatch |
| 3,837,339 A | 9/1974 | Aisenberg et al. |
| 4,585,652 A | 4/1986 | Miller et al. |
| 4,628,928 A | 12/1986 | Lowell |
| 4,714,460 A | 12/1987 | Calderon |
| 4,763,667 A | 8/1988 | Manzo |
| 4,771,772 A | 9/1988 | DeWitt |
| 4,817,601 A | 4/1989 | Roth et al. |
| 4,871,351 A | 10/1989 | Feingold |
| 4,905,689 A | 3/1990 | Stack et al. |
| 4,944,659 A | 7/1990 | Labbe et al. |
| 4,994,071 A | 2/1991 | MacGregor |
| 5,019,372 A | 5/1991 | Folkman et al. |
| 5,153,827 A | 10/1992 | Coutre et al. |
| 5,176,638 A | 1/1993 | Don Michael |
| 5,188,111 A | 2/1993 | Yates et al. |
| 5,234,457 A | 8/1993 | Andersen |
| 5,269,303 A | 12/1993 | Wernicke et al. |
| 5,279,607 A | 1/1994 | Schentag et al. |
| 5,310,404 A | 5/1994 | Gyory et al. |
| 5,314,451 A | 5/1994 | Mulier |
| 5,335,657 A | 8/1994 | Terry, Jr. et al. |
| 5,337,732 A | 8/1994 | Grundfest et al. |
| 5,338,625 A | 8/1994 | Bates et al. |
| 5,339,051 A | 8/1994 | Koehler et al. |
| 5,353,807 A | 10/1994 | DeMarco |
| 5,386,741 A | 2/1995 | Rennex |

(Continued)

FOREIGN PATENT DOCUMENTS

CN    99810271.7    10/2001

(Continued)

OTHER PUBLICATIONS

UK Intellectual Property Office Examination Report Under Section 18(3), App. No. GB0821523.8; Jul. 2, 2009; pp. 1-2.

(Continued)

*Primary Examiner*—Nicholas D Lucchesi
*Assistant Examiner*—Victoria P Campbell

(57) ABSTRACT

A system for perfusion management that monitors, maintains, diagnoses, or treats perfusion deficiencies.

21 Claims, 5 Drawing Sheets

U.S. PATENT DOCUMENTS

| | | | |
|---|---|---|---|
| 5,395,390 A | 3/1995 | Simon et al. |
| 5,398,670 A | 3/1995 | Ortiz et al. |
| 5,403,311 A | 4/1995 | Abele et al. |
| 5,411,551 A | 5/1995 | Winston et al. |
| 5,437,660 A | 8/1995 | Johnson et al. |
| 5,476,450 A | 12/1995 | Ruggio |
| 5,497,147 A | 3/1996 | Arms et al. |
| 5,522,394 A | 6/1996 | Zurbrugg |
| 5,551,953 A | 9/1996 | Lattin et al. |
| 5,554,914 A | 9/1996 | Miyazawa |
| 5,569,968 A | 10/1996 | Lal et al. |
| 5,574,347 A | 11/1996 | Neubauer |
| 5,593,434 A | 1/1997 | Williams |
| 5,599,324 A | 2/1997 | McAlister et al. |
| 5,610,488 A | 3/1997 | Miyazawa |
| 5,624,398 A | 4/1997 | Smith et al. |
| 5,632,754 A | 5/1997 | Farley et al. |
| 5,643,296 A | 7/1997 | Hundertmark et al. |
| 5,662,587 A | 9/1997 | Grundfest et al. |
| 5,669,874 A | 9/1997 | Feiring |
| 5,674,276 A | 10/1997 | Andersen et al. |
| 5,688,269 A | 11/1997 | Newton et al. |
| 5,695,457 A | 12/1997 | St. Goar et al. |
| 5,697,967 A | 12/1997 | Dinh et al. |
| 5,702,432 A | 12/1997 | Chen et al. |
| 5,705,293 A | 1/1998 | Hobson |
| 5,728,089 A | 3/1998 | Lal et al. |
| 5,737,279 A | 4/1998 | Carter |
| 5,782,798 A | 7/1998 | Rise |
| 5,804,563 A | 9/1998 | Still et al. |
| 5,807,395 A | 9/1998 | Mulier et al. |
| 5,819,736 A | 10/1998 | Avny et al. |
| 5,830,179 A | 11/1998 | Mikus et al. |
| 5,830,207 A | 11/1998 | Leeb et al. |
| 5,831,012 A | 11/1998 | Nilsson et al. |
| 5,843,139 A | 12/1998 | Goedeke et al. |
| 5,855,801 A | 1/1999 | Lin et al. |
| 5,873,835 A | 2/1999 | Hastings et al. |
| 5,908,027 A | 6/1999 | Butterfield et al. |
| 5,947,119 A | 9/1999 | Reznick |
| 5,951,600 A | 9/1999 | Lemelson |
| 5,954,675 A | 9/1999 | Dellagatta |
| 5,964,773 A | 10/1999 | Greenstein |
| 6,004,269 A | 12/1999 | Crowley et al. |
| 6,016,449 A | 1/2000 | Fischell et al. |
| 6,022,316 A | 2/2000 | Eppstein et al. |
| 6,053,873 A | 4/2000 | Govari et al. |
| 6,086,528 A | 7/2000 | Adair |
| 6,102,845 A | 8/2000 | Woodard et al. |
| 6,111,520 A | 8/2000 | Allen et al. |
| 6,128,538 A | 10/2000 | Fischell et al. |
| 6,134,474 A | 10/2000 | Fischell et al. |
| 6,159,230 A | 12/2000 | Samuels |
| 6,164,284 A | 12/2000 | Schulman et al. |
| 6,170,488 B1 | 1/2001 | Spillman, Jr. et al. |
| 6,179,789 B1 | 1/2001 | Tu et al. |
| 6,185,452 B1 | 2/2001 | Schulman et al. |
| 6,186,986 B1 | 2/2001 | Berg et al. |
| 6,187,599 B1 | 2/2001 | Asher et al. |
| 6,197,013 B1 | 3/2001 | Reed et al. |
| 6,219,577 B1 | 4/2001 | Brown, III et al. |
| 6,221,099 B1 | 4/2001 | Andersen et al. |
| 6,240,312 B1 | 5/2001 | Alfano et al. |
| 6,248,345 B1 | 6/2001 | Goldenheim et al. |
| 6,249,076 B1 | 6/2001 | Madden et al. |
| 6,255,361 B1 | 7/2001 | Rajagopalan et al. |
| 6,278,379 B1 | 8/2001 | Allen et al. |
| 6,295,990 B1 | 10/2001 | Lewis et al. |
| 6,296,638 B1 | 10/2001 | Davison et al. |
| 6,322,532 B1 | 11/2001 | D'Sa et al. |
| 6,337,997 B1 | 1/2002 | Rise |
| 6,372,248 B1 | 4/2002 | Qin et al. |
| 6,383,162 B1 | 5/2002 | Sugarbaker |
| 6,384,741 B1 | 5/2002 | O'Leary, Sr. |
| 6,385,472 B1 | 5/2002 | Hall et al. |
| 6,398,280 B1 | 6/2002 | Parker et al. |
| 6,402,678 B1 | 6/2002 | Fischell et al. |
| 6,409,674 B1 | 6/2002 | Brockway et al. |
| 6,436,120 B1 | 8/2002 | Meglin |
| 6,442,413 B1 | 8/2002 | Silver |
| 6,450,937 B1 | 9/2002 | Mercereau et al. |
| 6,464,687 B1 | 10/2002 | Ishikawa et al. |
| 6,475,639 B2 | 11/2002 | Shahinpoor et al. |
| 6,490,483 B2 | 12/2002 | Willis |
| 6,497,714 B1 | 12/2002 | Ishikawa et al. |
| 6,500,174 B1 | 12/2002 | Maguire et al. |
| 6,512,949 B1 | 1/2003 | Combs et al. |
| 6,512,950 B2 | 1/2003 | Li et al. |
| 6,514,237 B1 | 2/2003 | Maseda |
| 6,530,950 B1 | 3/2003 | Alvarado et al. |
| 6,547,825 B1 | 4/2003 | Shimizu et al. |
| 6,548,982 B1 | 4/2003 | Papanikolopoulos et al. |
| 6,554,798 B1 | 4/2003 | Mann et al. |
| 6,575,969 B1 | 6/2003 | Rittman, III et al. |
| 6,585,763 B1 | 7/2003 | Keilman et al. |
| 6,591,137 B1 | 7/2003 | Fischell et al. |
| 6,592,567 B1 | 7/2003 | Levin et al. |
| 6,597,954 B1 | 7/2003 | Pless et al. |
| 6,607,553 B1 | 8/2003 | Healy et al. |
| 6,616,676 B2 | 9/2003 | Bashiri et al. |
| 6,623,519 B2 | 9/2003 | Edwin et al. |
| 6,632,216 B2 | 10/2003 | Houzego et al. |
| 6,638,273 B1 | 10/2003 | Farley et al. |
| 6,648,908 B2 | 11/2003 | Dobak, III et al. |
| 6,666,860 B1 | 12/2003 | Takahashi |
| 6,669,683 B2 | 12/2003 | Santini, Jr. et al. |
| 6,673,042 B1 | 1/2004 | Samson et al. |
| 6,673,363 B2 | 1/2004 | Luo et al. |
| 6,679,893 B1 | 1/2004 | Tran |
| 6,709,388 B1 | 3/2004 | Mosse et al. |
| 6,711,423 B2 | 3/2004 | Colvin, Jr. |
| 6,712,835 B2 | 3/2004 | Mazzocchi et al. |
| 6,719,684 B2 | 4/2004 | Kim et al. |
| 6,735,474 B1 | 5/2004 | Loeb et al. |
| 6,735,475 B1 | 5/2004 | Whitehurst et al. |
| 6,743,211 B1 | 6/2004 | Prausnitz et al. |
| 6,754,536 B2 | 6/2004 | Swoyer et al. |
| 6,755,802 B2 | 6/2004 | Bell |
| 6,755,803 B1 | 6/2004 | Le et al. |
| 6,764,441 B2 | 7/2004 | Chiel et al. |
| 6,773,429 B2 | 8/2004 | Sheppard, Jr. et al. |
| 6,797,522 B1 | 9/2004 | Still et al. |
| 6,802,811 B1 | 10/2004 | Slepian |
| 6,824,508 B2 | 11/2004 | Kim et al. |
| 6,824,510 B2 | 11/2004 | Kim et al. |
| 6,824,561 B2 | 11/2004 | Soykan et al. |
| 6,849,183 B2 | 2/2005 | Gorsuch et al. |
| 6,855,115 B2 | 2/2005 | Fonseca et al. |
| 6,860,867 B2 | 3/2005 | Seward et al. |
| 6,861,001 B2 | 3/2005 | Lee et al. |
| 6,890,303 B2 | 5/2005 | Fitz |
| 6,898,464 B2 | 5/2005 | Edell et al. |
| 6,911,004 B2 | 6/2005 | Kim et al. |
| 6,911,496 B2 | 6/2005 | Rhee et al. |
| 6,920,359 B2 | 7/2005 | Meadows et al. |
| 6,921,413 B2 | 7/2005 | Mahadevan-Jansen et al. |
| 6,925,357 B2 | 8/2005 | Wang et al. |
| 6,929,636 B1 | 8/2005 | Von Alten |
| 6,936,003 B2 | 8/2005 | Iddan |
| 6,939,290 B2 | 9/2005 | Iddan |
| 6,939,376 B2 | 9/2005 | Shulze et al. |
| 6,950,707 B2 | 9/2005 | Whitehurst |
| 6,953,589 B1 | 10/2005 | Trautman et al. |
| 6,958,034 B2 | 10/2005 | Iddan |

| | | |
|---|---|---|
| 6,959,215 B2 | 10/2005 | Gliner et al. |
| 6,960,227 B2 | 11/2005 | Jones et al. |
| 6,963,792 B1 | 11/2005 | Green |
| 6,991,617 B2 | 1/2006 | Hektner et al. |
| 7,003,352 B1 | 2/2006 | Whitehurst |
| 7,013,177 B1 | 3/2006 | Whitehurst et al. |
| 7,037,343 B2 | 5/2006 | Imran |
| 7,042,184 B2 | 5/2006 | Oleynikov et al. |
| 7,101,386 B2 | 9/2006 | Dobak, III |
| 7,115,109 B2 | 10/2006 | Gerdts et al. |
| 7,125,382 B2 | 10/2006 | Zhou et al. |
| 7,131,979 B2 | 11/2006 | DiCarlo et al. |
| 7,160,258 B2 | 1/2007 | Imran et al. |
| 7,245,954 B2 | 7/2007 | Glukhovsky |
| 7,297,113 B1 | 11/2007 | Russell et al. |
| 7,341,577 B2 | 3/2008 | Gill |
| 7,365,509 B2 | 4/2008 | Park et al. |
| 7,383,071 B1 | 6/2008 | Russell et al. |
| 2001/0029348 A1 | 10/2001 | Willis |
| 2001/0051766 A1 | 12/2001 | Gazdzinski |
| 2002/0065509 A1 | 5/2002 | Lebel et al. |
| 2002/0068080 A1 | 6/2002 | Lerner |
| 2002/0090388 A1 | 7/2002 | Humes et al. |
| 2002/0116029 A1 | 8/2002 | Miller et al. |
| 2002/0116034 A1 | 8/2002 | Miller et al. |
| 2002/0147480 A1 | 10/2002 | Mamayek |
| 2002/0156462 A1 | 10/2002 | Stultz |
| 2002/0165592 A1 | 11/2002 | Glukhovsky et al. |
| 2002/0169436 A1 | 11/2002 | Gurm et al. |
| 2002/0188323 A1 | 12/2002 | Penner et al. |
| 2002/0193679 A1 | 12/2002 | Malave et al. |
| 2002/0193874 A1 | 12/2002 | Crowley |
| 2002/0198470 A1 | 12/2002 | Imran et al. |
| 2002/0198521 A1 | 12/2002 | Maguire |
| 2002/0198604 A1 | 12/2002 | Schulman et al. |
| 2003/0024534 A1 | 2/2003 | Silvestri et al. |
| 2003/0040704 A1 | 2/2003 | Dorros et al. |
| 2003/0065358 A1 | 4/2003 | Frecker et al. |
| 2003/0069475 A1 | 4/2003 | Banik et al. |
| 2003/0069523 A1 | 4/2003 | Williams et al. |
| 2003/0151524 A1 | 8/2003 | Clark |
| 2003/0152823 A1 | 8/2003 | Heller |
| 2003/0158584 A1 | 8/2003 | Cates et al. |
| 2003/0163177 A1 | 8/2003 | Eggers et al. |
| 2003/0167000 A1 | 9/2003 | Mullick et al. |
| 2003/0214579 A1 | 11/2003 | Iddan |
| 2003/0220556 A1 | 11/2003 | Porat et al. |
| 2004/0008853 A1 | 1/2004 | Pelrine et al. |
| 2004/0018508 A1 | 1/2004 | Friedman |
| 2004/0019374 A1 | 1/2004 | Hojeibane et al. |
| 2004/0064093 A1 | 4/2004 | Hektner et al. |
| 2004/0073177 A1 | 4/2004 | Hickle |
| 2004/0073190 A1 | 4/2004 | Deem et al. |
| 2004/0097819 A1 | 5/2004 | Duarte |
| 2004/0098030 A1 | 5/2004 | Makower et al. |
| 2004/0133147 A1 | 7/2004 | Woo |
| 2004/0147939 A1 | 7/2004 | Rabkin et al. |
| 2004/0148034 A1 | 7/2004 | Kagan et al. |
| 2004/0162469 A1 | 8/2004 | Imran |
| 2004/0162501 A1 | 8/2004 | Imran |
| 2004/0176664 A1 | 9/2004 | Iddan |
| 2004/0199246 A1 | 10/2004 | Chu et al. |
| 2004/0225325 A1 | 11/2004 | Bonutti |
| 2004/0225326 A1 | 11/2004 | Weiner et al. |
| 2004/0260391 A1 | 12/2004 | Santini, Jr. et al. |
| 2004/0267240 A1 | 12/2004 | Gross et al. |
| 2005/0004553 A1 | 1/2005 | Douk |
| 2005/0021023 A1 | 1/2005 | Guglielmi et al. |
| 2005/0027236 A1 | 2/2005 | Douk |
| 2005/0058701 A1 | 3/2005 | Gross et al. |
| 2005/0065592 A1 | 3/2005 | Holzer |
| 2005/0069925 A1 | 3/2005 | Ford et al. |
| 2005/0079132 A1 | 4/2005 | Wang et al. |
| 2005/0107870 A1 | 5/2005 | Wang et al. |
| 2005/0113460 A1 | 5/2005 | Glick |
| 2005/0121411 A1 | 6/2005 | Cohen |
| 2005/0126916 A1 | 6/2005 | Lockard et al. |
| 2005/0149170 A1 | 7/2005 | Van Tassel et al. |
| 2005/0151524 A1 | 7/2005 | Sae-Ueng et al. |
| 2005/0177223 A1 | 8/2005 | Palmaz |
| 2005/0182482 A1 | 8/2005 | Wang et al. |
| 2005/0203613 A1 | 9/2005 | Arney et al. |
| 2005/0216074 A1 | 9/2005 | Sahatjian et al. |
| 2005/0221529 A1 | 10/2005 | Bang et al. |
| 2005/0228259 A1 | 10/2005 | Glukhovsky et al. |
| 2005/0234393 A1 | 10/2005 | Wood, Jr. |
| 2005/0234398 A1 | 10/2005 | Wood, Jr. |
| 2005/0234399 A1 | 10/2005 | Wood, Jr. |
| 2005/0234440 A1 | 10/2005 | Wood, Jr. |
| 2005/0238689 A1 | 10/2005 | Carpenter et al. |
| 2005/0272806 A1 | 12/2005 | Falotico et al. |
| 2005/0272974 A1 | 12/2005 | Iddan |
| 2005/0277839 A1 | 12/2005 | Alderman et al. |
| 2005/0278020 A1 | 12/2005 | Wang et al. |
| 2006/0004395 A1 | 1/2006 | Chiel et al. |
| 2006/0009810 A1 | 1/2006 | Mann et al. |
| 2006/0015146 A1 | 1/2006 | Girouard et al. |
| 2006/0069425 A1 | 3/2006 | Hillis et al. |
| 2006/0074479 A1 | 4/2006 | Bailey et al. |
| 2006/0119304 A1 | 6/2006 | Farritor et al. |
| 2006/0167339 A1 | 7/2006 | Gilad et al. |
| 2007/0010868 A1 | 1/2007 | Ferren et al. |
| 2007/0066929 A1 | 3/2007 | Ferren et al. |
| 2007/0088334 A1 | 4/2007 | Hillis et al. |
| 2007/0225634 A1 | 9/2007 | Ferren et al. |
| 2008/0063703 A1 | 3/2008 | Gross et al. |

FOREIGN PATENT DOCUMENTS

| | | | |
|---|---|---|---|
| EP | 1 245 201 | A1 | 10/2002 |
| EP | 1 618 831 | A2 | 1/2006 |
| EP | 2 163 206 | A1 | 3/2010 |
| JP | 2005-74229 | | 3/2005 |
| WO | WO 96/39999 | | 12/1996 |
| WO | WO 98/14243 | | 4/1998 |
| WO | WO 99/20335 | | 4/1999 |
| WO | WO 99/44665 | | 9/1999 |
| WO | WO 00/69515 | | 11/2000 |
| WO | WO 03/072157 | A1 | 9/2003 |
| WO | WO 03/090618 | A2 | 11/2003 |
| WO | WO 03/106966 | A2 | 12/2003 |
| WO | WO 2004/028335 | A2 | 4/2004 |
| WO | WO 2004/058041 | A2 | 7/2004 |
| WO | WO 2004/086958 | A1 | 10/2004 |
| WO | WO 2005/082248 | A1 | 9/2005 |

OTHER PUBLICATIONS

U.S. Appl. No. 11/651,946, Ferren et al.
U.S. Appl. No. 11/645,358, Ferren et al.
U.S. Appl. No. 11/645,357, Ferren et al.
U.S. Appl. No. 11/485,619, Hillis et al.
U.S. Appl. No. 11/478,368, Ferren et al.
U.S. Appl. No. 11/417,898, Hillis et al.
U.S. Appl. No. 11/403,230, Ferren et al.
U.S. Appl. No. 10/949,186, Hillis et al.
PCT International Search Report; International App. No. PCT/US2007/008993; Sep. 29, 2008; pp. 1-3.
PCT International Search Report; International App. No. PCT/US07/10819; Aug. 27, 2008; pp. 1-3.
PCT International Search Report; International App. No. PCT/US07/10824; Aug. 21, 2008; pp. 1-3.
PCT International Search Report; International App. No. PCT/US07/10942; Aug. 15, 2008; pp. 1-3.
PCT International Search Report; International App. No. PCT/US07/10936; Jul. 24, 2008; pp. 1-3.

PCT International Search Report; International App. No. PCT/US07/10857; Jul. 21, 2008; pp. 1-2.
PCT International Search Report; International App. No. PCT/US07/10969, Nov. 10, 2008; pp. 1-2.
PCT International Search Report; International App. No. PCT/US2007/008993; Sep. 30, 2008; pp. 1-3.
U.S. Appl. No. 12/075,480, Hillis et al.
U.S. Appl. No. 11/891,573, Wood, Jr., Lowell L.
U.S. Appl. No. 11/891,371, Wood, Jr., Lowell L.
U.S. Appl. No. 11/891,356, Wood, Jr., Lowell L.
U.S. Appl. No. 11/891,355, Wood, Jr., Lowell L.
U.S. Appl. No. 11/891,333, Wood, Jr., Lowell L.
U.S. Appl. No. 11/726,031, Ferren et al.
U.S. Appl. No. 11/726,025, Ferren et al.
U.S. Appl. No. 11/725,982, Ferren et al.
UK Intellectual Property Office Examination Report Under Section 18(3); App. No. GB0706802.6; bearing a date of Dec. 1, 2008; pp. 1-2.
PCT International Search Report; International App. No. PCT/US05/13349; Apr. 28, 2008; pp. 1-2.
"001_08 Comparison of Capsule Cameras: M2A (Given Imaging) vs. NORIKA3 (RF System lab)" RF System lab; bearing dates of 2001-2004; pp. 1-2; http://www.rfnorika.com/eng/system/sys_008.html; printed on May 4, 2006.
"A Hydrogel-based CO2 sensor"; BIOS—The lab on a chip group; bearing a date of Aug. 29, 2005; pp. 1-2; http://bios.ewi.utwente.nl/research/analysissystemssenors/ahydrogelbased.doc/index.html; printed on Apr. 25, 2006; University of Twente; the Netherlands.
Agarwal, Abhishek K.; Atencia, Javier; Beebe, David J.; Jiang, Hongrui; "Magnetically-driven temperature-controlled microfluidic actuators"; pp. 1-5; http://www.unl.im.dendai.ac.jp/INSS2004/INSS2004_papers/OralPresentations/C2.pdf.
"Agile new plastics change shape with heat"; MIT News Office; Nov. 20, 2006; pp. 1-4; Massachusetts Institute of Technology; printed on Nov. 22, 2006; http://web.mit.edu/newsoffice/2006/triple-shape.html.
"Agile new plastics change shape with heat"; MIT Tech Talk; Nov. 22, 2006; p. 5 (1 page).
Ananthaswamy, Anil; "First robot moved by muscle power"; bearing a date of Feb. 27, 2004; pp. 1-3; New Scientist; http://www.newscientist.com/article.ns?id=dn4714; printed on Sep. 12, 2006.
Asari, Vijayan K.; Kumar, Sanjiv; Kassim, Irwan M.; "A Fully Autonomous Microrobotic Endoscopy System"; Journal of Intelligent and Robotic Systems; bearing a date of 2000; pp. 325-341; vol. 28; Kluwer Academic Publishers.
Behkam, Bahareh; Sitti, Metin; "Towards Hybrid Swimming Microrobots: Bacteria Assisted Propulsion of Polystyrene Beads"; Proceedings of the 28th IEEE EMBS Annual International Conference; bearing dates of Aug. 30, 2006-Sep. 3, 2006 and 2006; pp. 2421-2424; IEEE.
Berlinger, Norman T.; "Robotic Surgery—Squeezing into Tight Places"; New England Journal of Medicine; bearing dates of May 17, 2006, May 18, 2006, and 2006; pp. 2099-2101; Massachusetts Medical Society; www.nejm.org.
Bezrouk, A.; Hanuš, J.; Záhora, J.; "Temperature Characteristics of Nitinol Spiral Stents";Scripta Medica (BRNO); bearing dates of Aug. 2005, Oct. 2005; pp. 219-226; vol. 78, No. 4.
Bialek, William; Rieke, Fred; De Ruyter Van Steveninck, Rob R.; Warland, David; "Reading a Neural Code"; Science; bearing a date of Jun. 28, 1991; pp. 1854-1857; vol. 252.
Bucher, Volker; Graf, Michael; Stelzle, Martin; Nisch, Wilfried; "Low-Impedance Thin-Film Polycrystalline Silicon Microelectrodes for Extracellular Stimulation and Recording"; Biosensors and Bioelectronics; bearing a date of 1999; pp. 639-649; vol. 14; Elsevier Science S.A.; www.elsevier.com/locate/bios.
Butson, Christopher R.; McIntyre, Cameron C.; "Role of Electrode Design on the Volume of Tissue Activated During Deep Brain Stimulation"; Journal of Neural Engineering; bearing a date of 2006; vol. 3; pp. 1-8; IOP Publishing Ltd.
Chang, Suk Tai; Paunov, Vesselin N.; Petsev, Dimiter N.; Velev, Orlin D.; "Articles: Remotely Powered Self-Propelling Particles and Micropumps Based on Miniature Diodes"; Nature Materials; bearing a date of 2007; pp. 1-6; Nature Publishing Group; www.nature.com/naturematerials.
Chen, Haitao; Ebner, Armin D.; Ritter, James A.; Kaminski, Michael D.; Rosengart, Axel J.; "Sequestration of Blood-Borne Magnetic Drug Carrier Particles Using Magnetizable Intravascular Stents"; Collaborative Investigators for Applied Nanotechnology in Medicine; pp. 1; Chicago, Illinois.
Chen, Ting; Barton, Scott Calabrese, Binyamin, Gary; Gao, Zhiqiang; Zhang, Yongchao, Kim, Hyug-Han; Heller, Adam; "A Miniature Biofuel Cell"; Journal of the American Chemical Society; Aug. 11, 2001; pp. 8630-8631; vol. 123; 2001 American Chemical Society.
Christensen, Bill; "Musclebot: Microrobot with a Heart"; Technovelgy.com; pp. 1-2; bearing a date of Feb. 27, 2004; http://www.technovelgy.com/ct/Science-Fiction-News.
asp?NewsNum=46; printed on Sep. 12, 2006.
Christensen, Bill; "Propulsion System for 'Fantastic Voyage' Robot"; Technovelgy.com; pp. 1-4; Technovelgy.com; located http://www.technovelgy.com/ct/Science-Fiction-News.asp?NewsNum=811; printed on Jan. 4, 2007.
Costamagna; Guido M.D.; "PillCam™ SB Capsule Endoscopy"; Given Imaging.com; bearing dates of 2001-2006; pp. 1-4; http://www.givenimaging.com/Cultures/en-US/Given/English/Products/CapsuleEndoscopy/; printed on May 4, 2006.
Cui, Xinyan; Hetke, Jamille F.; Wiler, James A.; Anderson, David J.; Martin, David.; "Electrochemical Deposition and Characterization of Conducting Polymer Polypyrrole/PPS on Multichannel Neural Probes" ; Sensors and Actuators A Physical; bearing a date of 2001; pp. 8-18; vol. 93; Elsevier Science B.V.; www.elsevier.com/locate/sna.
Dario, P.; Carrozza, M.C.; Lencioni, L.; Magnani, B.; D'Attanasio, S.; "A Micro Robotic System for Colonoscopy"; Proceedings of the 1997 IEEE International Conference on Robotics and Automation; bearing dates of Apr. 1997 and 1997; pp. 1567-1572; IEEE.
Dillier, Norbert; Lai, Wai Kong; Almqvist, Bengt; Frohne, Carolin; Müller-Deile, Joachim; Stecker, Matthias; Von Wallenberg, Ernst; "Measurement of the Electrically Evoked Compound Action Potential Via a Neural Response Telemetry System"; Annals of Otology Rhinology and Laryngology; bearing a date of May 2002; pp. 407-414; vol. 111, No. 5; Annals Publishing Company.
Dongxiang, Chi; Guozheng, Yan; "An earthworm based miniature robot for intestinal inspection"; Proceedings of SPIE; bearing dates of Nov. 7, 2001-Nov. 9, 2001; pp. 396-400; vol. 4601; SPIE.
Donoghue, John P.; "Review: Connecting Cortex to Machines: Recent Advances in Brain Interfaces"; Nature Neuroscience Supplement; bearing a date on Nov. 2002; pp. 1085-1088; vol. 5; Nature Publishing Group; http://www.nature.com/natureneuroscience.
Fang, Zi-Ping; Mortimer, J. Thomas; "Selective Activation of Small Motor Axons by Quasitrapezoidal Current Pulses"; IEEE Transactions on Biomedical Engineering; bearing a date of Feb. 1991; pp. 168-174; vol. 38, No. 2; IEEE.
Fiaccabrino, G.C.; Tang, X.-M.; Skinner, N.; De Rooij, N.F.; Koudelka-Hep, M.; "Electrochemical Characterization of Thin-Film Carbon Interdigitated Electrode Arrays"; Analytica Chimica Acta; bearing a date of 1996; pp. 155-160; vol. 326; Elsevier Science B.V.
Freitas Jr., Robert A.; "8.2.1.2 Arteriocenous Microcirculation"; "9.4.3.5 Legged Ambulation"; "9.4.3.6 Tank-Tread Rolling"; "9.4.3.7 Amoeboid Locomotion"; "9.4.3.8 Inchworm Locomotion"; "Nanomedicine vol. I: Basic Capabilities"; bearing a date of 1999; pp. 211-214, pp. 316-318; Landes Bioscience; Georgetown, Texas, USA.
Gitter, Alfred H.; Fromm, Michael; Schulzke, Jörg-Dieter; "Impedance Analysis for the Determination of Epithelial and Subepithelial Resistance in Intestinal Tissues"; Journal of Biochemical and Biophysical Methods; bearing a date of 1998; pp. 35-46; vol. 37; Elsevier Science B.V.
Goda, Yukiko; Colicos, Michael A.; "Protocol: Photoconductive Stimulation of Neurons Cultured on Silicon Wafers"; Nature Protocols; bearing a date of 2006; pp. 461-467; vol. 1, No. 1; Nature Publishing Group; http://www.nature.com/natureprotocols.

Gozani, Shai N.; Miller, John P.; "Optimal Discrimination and Classification of Neuronal Action Potential Waveforms from Multiunit, Multichannel Recordings Using Software-Based Linear Filters"; IEEE Transactions on Biomedical Engineering; bearing a date of Apr. 1994; pp. 358-372; vol. 41, No. 4; IEEE.

Gray, Charles M.; Maldonado, Pedro E.; Wilson, Mathew; McNaughton, Bruce; "Tetrodes Markedly Improve the Reliability and Yield of Multiple Single-Unit Isolation from Multi-Unit Recordings in Cat Striate Cortex"; Journal of Neuroscience Methods; bearing a date of 1995; pp. 43-54; vol. 63; Elsevier Science B.V.

Hagleitner, C.; Hierlemann, A.; Lange, D.; Kummer, A.; Kerness, N.; Brand, O.; Baltes, H.; "Smart single-chip gas sensor microsystem"; Nature; Nov. 15, 2001; pp. 293-296; vol. 414; Macmillan Magazines Ltd.; www.nature.com.

Hanna, Darrin M.; Oakley, Barbara A.; Stryker, Gabrielle A.; "Using a System-on-Chip Implantable Device to Filter Circulating Infected Cells in Blood or Lymph"; IEEE Transactions on Biomedical Engineering; bearing dates of Jan. 25, 2003, Mar. 2003; pp. 6-13; vol. 2, No. 1; IEEE.

Hodgkin, A.L.; Huxley, A.F.; "A Quantitative Description of Membrane Current and its Application to Conduction and Excitation in Nerve"; Journal of Physiology; bearing a date of 1952; pp. 500-544; vol. 117.

Høeg, H.D.; Slatkin, A.B.; Burdick, J.W.; Grundfest, Dr. Warren S.; "Biomechanical Modeling of the Small Intestine as Required for the Design and Operation of a Robotic Endoscope"; Proceedings ICRA '00 IEEE International Conference on Robotics and Automation; Apr. 24, 2000-Apr. 28, 2000; pp. 1-8; vol. 2.

Hofmann, U.G.; Folkers, A.; Mösch, F.; Höhl, D.; Kindlundh, M.; Norlin, P.; "A 64(128)-Channel Multisite Neuronal Recording System"; bearing a date of 2002; pp. 1-4.

Ikeuchi, K.; Yoshinaka, K.; Hashimoto, S.; Tomita, N.; "Locomotion of Medical Micro Robot with Spiral Ribs Using Mucus"; Seventh International Symposium on Micro Machine and Human Science; bearing a date of 1996; pp. 217-222; IEEE.

Inmann, Andreas; Haugland, Morten; Haase, Jens; Biering-Sørensen, Fin; Sinkjaer, Thomas; "NeuroReport: Signals from Skin Mechanoreceptors used in Control of a Hand Grasp Neuroprosthesis"; Motor Systems; bearing a date of Sep. 17, 2001; pp. 2817-2819; vol. 12, No. 13; Lippincott Williams & Wilkins.

Janders, M.; Egert, U.; Stelze, M.; Nisch, W.; "Novel Thin Film Titanium Nitride Micro-Electrodes with Excellent Charge Transfer Capability for Cell Stimulation and Sensing Applications"; IEEE Engineering in Medicine and Biology Society; bearing a date of 1996; pp. 245-247; IEEE.

"Japanese Researchers Unveil Medical Mini Robot"; Yahoo! News; bearing a date of Mar. 8, 2007; pp. 1-2; Yahoo! Inc.; http://news.yahoo.com/s/afp/20070308/hl_afp/afplifestyleshealthscience; printed on Mar. 8, 2007.

Ji, Jin; Najafi, Khalil; Wise, Kensall D.; "A Low-Noise Demultiplexing System for Active Multichannel Microelectrode Arrays"; IEEE Transactions of Biomedical Engineering; bearing a date of Jan. 1991; pp. 77-81; vol. 38, No. 1; IEEE.

Kassim, Irwan; Phee, Louis; NG, Wan S.; Gong, Feng; Dario, Paolo; Mosse, Charles A.; "Locomotion Techniques for Robotic Colonoscopy"; IEEE Engineering in Medicine and Biology Magazine; bearing dates of May/Jun. 2006 and 2006; pp. 49-56; IEEE.

Kennedy, P.R.; Bakay, R.A.E.; Moore, M.M.; Adams, K.; Goldwaithe, J.; "Direct Control of a Computer from the Human Central Nervous System"; IEEE Transactions on Rehabilitation Engineering; bearing a date of Jun. 2000; pp. 198-202; vol. 8, No. 2; IEEE.

Kobetic, Rudi; Triolo, Ronald J.; Uhlir, James P.; Bieri, Carole; Wibowo, Michael; Polando, Gordie; Marsolais, E. Byron; Davis Jr., John A.; Ferguson, Kathleen A.; Sharma, Mukut; "Implanted Functional Electrical Stimulation System for Mobility in Paraplegia: A Follow-Up Case Report"; IEEE Transactions on Rehabilitation Engineering; bearing a date of Dec. 1999; pp. 390-398; vol. 7, No. 4; IEEE.

Krueger, Curtis; "New light on blood testing"; Oct. 20, 2006; pp. 1-2; St. Petersburg Times; printed on Oct. 24, 2006; located at http://www.sptimes.com/2006/10/20news_pf/Tampabay/New_light_on_blood_te.shtml.

Langer, Robert; Peppas, Nicholas A.; Advances in Biomaterials, Drug Delivery, and Bionanotechnology;; AIChE Journal—Bioengineering, Food, and Natural Products; Dec. 2003; pp. 2990-3006; vol. 49, No. 12.

Loeb, G.E.; Peck, R.A.; Martyniuk, J.; "Toward the Ultimate Metal Microelectrode"; Journal of Neuroscience Methods; bearing a date of 1995; pp. 175-183; vol. 63; Elsevier Science B.V.

Loeb, Gerald E.; Peck, Raymond A.; Moore, William H.; Hood, Kevin; "BION System for Distributed Neural Prosthetic Interfaces"; Medical Engineering and Physics; bearing a date of 2001; pp. 9-18; vol. 23; Elsevier Science Ltd.; www.elsevier.com/locate/medengphy.

Lu, Zhao; Martel, Sylvain; "Preliminary Investigation of Bio-carriers Using Magnetotactic Bacteria"; Proceedings of the $28^{th}$ IEEE EMBS Annual International Conference; bearing dates of Aug. 30, 2006-Sep. 3, 2006 and 2006; pp. 3415-3418; IEEE.

Mangan, Elizabeth V.; Kingsley, Dan A.; Quinn, Roger D.; Chiel, Hillel J.; "Development of a Peristaltic Endoscope"; IEEE International Conference on Robotics & Automation 2002; pp. 1-6; http://biorobots.cwru.edu/publications/ICRA02_Mangan_Endoscope.pdf.

Marks, William B.; Loeb, Gerald E.; "Action Currents, Internodal Potentials, and Extracellular Records of Myelinated Mammalian Nerve Fibers Derived from Node Potentials"; Biophysical Journal; 1976; pp. 655-668; vol. 16.

Martel, Sylvain; "Fundamentals of high-speed piezo-actuated three-legged motion for miniature robots designed for nanometer-scale operations"; pp. 1-8.

Martel, Sylvain; "Towards MRI-Controlled Ferromagnetic and MC-1 Magnetotactic Bacterial Carriers for Targeted Therapies in Arteriolocapillar Networks Stimulated by Tumoral Angiogenesis"; Proceedings of the $28^{th}$ IEEE EMBS Annual International Conference; bearing dates of Aug. 30, 2006-Sep. 3, 2006 and 2006; pp. 3399-3402; IEEE.

Martel, Sylvain; Mathieu, Jean-Baptiste; Felfoul, Ouajdi; Chanu, Arnaud; Aboussouan, Eric; Tamaz, Samer; Pouponneau, Pierre; "Automatic Navigation of an Untethered Device in the Artery of a Living Animal using a Conventional Clinical Magnetic Resonance Imaging System"; Applied Physics Letters; 2007; pp. 114105-1-114105-3; vol. 90, No. 114105; American Institute of Physics.

Mathieu, J-B.; Martel, S.; Yahia, L'H.; Soulez, G.; Beaudoin, G.; "MRI Systems as a Mean of Propulsion for a Microdevice in Blood Vessels"; bearing a date of 2003; pp. 3419-3422; IEEE.

Matsui, Takemi; Matsumura, Kouji; Hagisawa, Kousuke; Ishihara, Masayuki; Ishizuka, Toshiaki; Suzuki, Minoru; Kurita, Akira; Kikuchi, Makoto; "A Novel Ferromagnetic Thermo-Stent for Plaque Stabilization That Self-Regulates the Temperature"; IEEE Transactions on Biomedical Engineering; bearing dates of Jun. 2002 and 2002; pp. 621-623; vol. 49, No. 6; IEEE.

McNeal, Donald R.; "Analysis of a Model for Excitation of Myelinated Nerve"; IEEE Transactions on Biomedical Engineering; bearing a date of Jul. 1976; pp. 329-337; vol. BME-23, No. 4.

Meier, P.; Oberthür, S.; Lang, M.; "Development of a compliant device for minimally invasive surgery"; Proceedings of the $28^{th}$ IEEE EMBS Annual International Conference; bearing dates of Aug. 30, 2006-Sep. 3, 2006 and 2006; pp. 331-334; IEEE.

"MEMS at the cutting edge®, Patent Pending"; Verimetra; pp. 1-2; http://www.verimetra.com/flow.htm; printed on May 4, 2006.

Menciassi, A.; Park, Jong H.; Lee, S.; Gorini, S.; Dario, P.; Park, Jong-oh; "Robotic Solutions and Mechanisms for a Semi-Autonomous Endoscope"; Proceedings of the 2002 IEEE/RSJ International Conference on Intelligent Robots and Systems; bearing a date of 2002; pp. 1379-1384; IEEE.

Mohseni, Kamran; "Biomimetic & Bio-Inspired Aerial and Underwater Vehicles"; bearing a date of Sep. 23, 2006; pp. 1-10; printed on Jan. 4, 2007; http://enstrophy.colorado.edu/~mohseni/MicroVehicles1.html#UUV1#UUV1.

Mosse, Charles; Mills, Tim; Appleyard, Mark; Swain, Paul; "Electrostimulation to move endoscopes in the small bowel"; Proceedings of SPIE; bearing a date of 2001; pp. 24-28; vol. 4158.

Murthy, S. Narasimha; Hiremath, Shobha Rani R.; "Physical and Chemical Permeation Enhancers in Transdermal Delivery of Terbutaline Sulphate"; AAPS PharmSciTech; bearing a date of 2001; pp. 1-5; vol. 2001, 2(1); Technical Note 1; http://www.pharmscitech.com/.

Nakayama, Yasuhide; Ji-Youn, Kim; Nishi, Shogo; Ueno, Hikaru; Matsuda, Takehisa; "Development of high-performance stent: gelatinous photogel-coated stent that permits drug delivery and gene transfer"; J Biomed Mater Res; bearing dates of Nov. 13, 2000, Apr. 23, 2001, May 10, 2001 and 2001; pp. 559-566; vol. 57; John Wiley & Sons, Inc.

Naqvi, Nasir H.; Rudrauf, David; Damasio, Hanna; Bechara, Antoine; "Damage to the Insula Disrupts Addiction to Cigarette Smoking"; Science; bearing a date of Jan. 26, 2007; pp. 531-534; vol. 315, No. 531; www.sciencemag.org; printed on Jan. 25, 2007.

Neto, A.M. Figueiredo; Godinho, M.H.; Toth-Katona, T.; Palffy-Muhoray, P.; "Optical, Magnetic and Dielectric Properties of Non-Liquid Crystalline Elastomers Doped with Magnetic Colloids"; Brazilian Journal of Physics; Bearing a date of Mar. 2005; pp. 184-189; vol. 35, No. 1.

"New Medical Device Combines Wireless and MEMS Technology"; Georgia Institute of Technology; pp. 1-4; PhysOrg.com; http://www.physorg.com/.printnews.php?newsid=10533; printed on Feb. 20, 2006.

Nieuwenhuizen-Berkovits, P.; "lubrelastic medical appliances"; Lubrelastic Medical Appliances; pp. 1-4; http://www.xs4a11.nl/~plien070/caeng.html; printed on Feb. 20, 2006.

Nyitrai, Zsolt; Illyefalvi-Vitéz, Zsolt; Pinkola, János; "Preparing Stents with Masking & Etching Technology"; 26th International Spring Seminar on Electronics Technology; bearing dates of May 8, 2003-May 11, 2003 and 2003; pp. 321-324; IEEE.

Olsson III, R.H.; Gulari, M.N.; Wise, K.D.; "Poster 114: Silicon Neural Recording Arrays with On-Chip Electronics for In-Vivo Data Acquisition"; Microtechnologies in Medicine and Biology; bearing dates of May 2, 2002-May 4, 2002; pp. 237-240; IEEE.

Oweiss, Karim G.; Anderson, David J.; "A New Technique for Blind Source Separation Using Subband Subspace Analysis in Correlated Multichannel Signal Environments"; bearing a date of 2001; pp. 2813-2816; IEEE.

Patronik, N.A.; Ota, T.; Zenati, M.A.; Riviere, C.N.; "Improved Traction for a Mobile Robot Traveling on the Heart"; Proceedings of the 28th IEEE EMBS Annual International Conference; bearing dates of Aug. 30, 2006-Sep. 3, 2006 and 2006; pp. 339-342; IEEE.

PCT International Search Report App. No. PCT/US05/33475; dated Sep. 5, 2006; pp. 1-2.

Peckham, P. Hunter; Knutson, Jayme S.; "Functional Electrical Stimulation for Neuromuscular Applications"; Annual Review Biomedical Engineering; bearing a date of 2005; pp. 327-360; vol. 7; Annual Reviews.

Rattay, F.; "The Basic Mechanism for the Electrical Stimulation of the Nervous System"; Neuroscience; 1999; pp. 335-346; vol. 98. No. 2; Elsevier Science Ltd; printed on Mar. 15, 2007.

Rattay, Frank, Aberham, Matthias; "Modeling Axon Membranes from Functional Electrical Stimulation"; IEEE Transactions on Biomedical Engineering; bearing a date of Dec. 1993; pp. 1201-1209; vol. 40, No. 12; IEEE.

Rattay, Frank; "Analysis of Models for Extracellular Fiber Stimulation"; IEEE Transactions on Biomedical Engineering; bearing a date of Jul. 1989; pp. 676-682; vol. 36, No. 7; IEEE.

"Remote-Control Electrostimulation Capsule", Popular Science; bearing dates of 2002 and 2003; pp. 1-2; http://www.popsci.com/popsci/brown/2003/article/0,18881,537028.00.html; printed on May 4, 2006.

"Researchers: Squid-Inspired Vortex Generators Could Mean Better Propulsion for Unmanned Underwater Vehicles"; UnderwaterTimes.com; Dec. 12, 2006; pp. 1-2; UnderwaterTimes.com; printed on Jan. 4, 2007; http://www.underwatertimes.com/print.php?article_id=51030782641.

Rice, Mike; "Implantable Neurostimulation Device Market Poised for Explosive Growth"; Future Fab International; Jan. 7, 2006; pp. 1-4; printed on Oct. 6, 2006; http://www.future-fab.com/documents.asp?d_ID=3725.

Rice, Mike; "New Products, Emphasis on Miniaturization Driving Medical Device Innovation"; bearing a date Aug. 23, 2006; pp. 1-3; Advantage Business Media; http://www.mdtmag.com/scripts/ShowPR.asp?PUBCODE=046&ACCT=0006109&ISSUE=0603&RELTYPE=PR&PRODUCE=0790&PRODLETT=A; printed on Aug. 23, 2006.

Riedmüller, J.; Bolz, A.; Rebling, H.; Schaldach, M.; "Improvement of Stimulation and Sensing Performance of Bipolar Pacemaker Leads"; IEEE Eng. Med. Biol. Soc.; 1992; pp. 2364-2365; IEEE.

Robinson, David A.; "The Electrical Properties of Metal Microelectrodes"; Proceedings of the IEEE; bearing a date of Jun. 1968; pp. 1065-1071; vol. 56, No. 6.

Rousche, Patrick J.; Pellinen, David S.; Pivin, David P.; Williams, Justin C.; Vetter, Rio J.; Kipke, Daryl R.; "Flexible Polyimide-Based Intracortical Electrode Arrays with Bioactive Capability"; IEEE Transactions on Biomedical Engineering; bearing a date Mar. 2001; pp. 361-371; vol. 48, No. 3; IEEE.

Rutten, Wim; Mouveroux, Jean-Marie; Buitenweg, Jan; Heida, Ciska; Ruardij, Teun; Marani, Enrico; Lakke, Egbert; "Neuroelectronic Interfacing with Cultured Multielectrode Arrays Toward a Cultured Probe"; Proceedings of the IEEE; bearing a date of Jul. 2001; pp. 1013-1029; vol. 89, No. 7; IEEE.

Saltzman, John R.; "Endoscopic Advances—A View Toward the Future"; bearing dates of May 4, 2006, May 17, 2005, and 2005; pp. 1-4; Medscape; http://www.medscape.com/viewarticle/505100; printed on May 4, 2006.

Schmidt, W.; Behrens, P.; Behrend, D.; Schmitz, K.-P.; Andresen, R.; "Experimental Study of Peripheral, Balloon-expandable Stent Systems"; Progress in Biomedical Research; bearing a date of May 2001; pp. 246-255.

Schoonhoven, R.; Stegeman, D.F.; "Models and Analysis of Compound Nerve Action Potentials"; Critical Reviews in Biomedical Engineering; bearing a date of 1991; pp. 47-111; vol. 19, No. 1; CRC Press, Inc.

Senel, Sevda; Hincal, A. Atilla; "Drug permeation enhancement via buccal route: possibilities and limitations"; Journal of Controlled Release; bearing a date of 2001; pp. 133-144; vol. 72 (2001); Elsevier; www.elsevier.com/locate/jconrel.

Serruya, Mijail D.; Hatsopoulos, Nicholas G.; Paninski, Liam; Fellows, Matthew R.; Donoghue, John P.; "Brief Communications: Instant Neural Control of a Movement Signal"; Nature; bearing a date of Mar. 14, 2002; pp. 141-142; vol. 416; Macmillan Magazines Ltd; www.nature.com.

Serruys, Patrick W.; Kutryk, Michael J.B.; Ong, Andrew T.L.; "Coronary-Artery Stents"; The New England Journal of Medicine; bearing dates of Feb. 2, 2006 and Feb. 15, 2006; pp. 483-495; vol. 354;5; Massachusetts Medical Society.

Shabalovskaya, Svetlana, A.; "Surface, corrosion and biocompatibility aspects of Nitinol as an implant material"; Bio-Medical Materials and Engineering; bearing dates of Apr. 4, 2001, and 2002; pp. 69-109; vol. 12; IOS Press.

Shahinpoor, Mohsen; Kim, Kwang J.; Ionic polymer-metal composites: IV. Industrial and medical applications; Smart Materials and Structures; 2005; pp. 197-214; vol. 14; Institute of Physics Publishing.

Smith, Michael; "PAS: Nasal Spray Flu Vaccine Seems Safe and Effective in Young"; May 2, 2006; pp. 1-2; MedPage Today, LLC; bearing dates of 2004-2006; printed on May 4, 2006; http://www.medpagetoday.com/tbprint.cfm?tbid=3213.

Snoek, GJ; Ijzerman, MJ; in 'T Groen, FACG; Stoffers, TS; Zilvold, G; "Use of the NESS Handmaster to Restore Handfunction in Tetraplegia: Clinical Experiences in Ten Patients"; Spinal Cord; bearing a date of 2000; pp. 244-249; vol. 38; International Medical Society of Paraplegia.

Snow, E.S.; Perkins, F.K.; Houser, E.J.; Badescu, S.C.; Reinecke, T. L.; "Chemical Detection with a Single-Walled Carbon Nanotube Capacitor"; Science; Mar. 25, 2005; pp. 1942-1945; vol. 307; www.sciencemag.org.

Stoeckel, Dieter; Pelton, Alan; Duerig, Tom; "Self-expanding nitinol stents: material and design considerations"; European Radiology; bearing dates of Jan. 28, 2003, May 22, 2003, Jul. 1, 2003, Sep. 3, 2003, Feb. 2004 and 2004; pp. 292-301(1-2); vol. 14, No. 2; Springer-Verlang GmbH-SpringerLink—Article; http://www.springerlink.com/(1begg455gtgjfseqqptyb43m)/app/home/contribution.asp?referrer=parent&backto=issue,17,26;journal,27,147;browsepublicationresults,444,1551; printed on Feb. 22, 2006.

Strauss, Bradley H., M.D., Ph.D.; Li, Chris, M.D.; Whittingham, Heather A., M.Sc; Tio, Fermin O., M.D.; Kutryk, Michael J.B., M.D., Ph.D.; Janicki, Christian, Ph.D.; Sparkes, John, D., M.Sc.; Turnlund, Todd, B.Sc.; Sweet, William L., M.D.; "Late Effects of Low-Energy Gamma-Emitting Stents in a Rabbit Iliac Artery Model"; Int. J. Radiation Oncology Biol. Phys.; bearing dates of Oct. 23, 2001, May 13, 2002 and May 15, 2002 and 2002; pp. 551-561; vol. 54, No. 2; Elsevier Science Inc.

Struijk, Johannes Jan; "The Extracellular Potential of a Myelinated Nerve Fiber in an Unbounded Medium and in Nerve Cuff Models"; Biophysical Journal; bearing a date of Jun. 1997; pp. 2457-2469; vol. 72; Biophysical Society.

Taylor, Dawn M.; Helms Tillery, Stephen I.; Schwartz, Andrew B.; "Research Article: Direct Cortical Control of 3D Neuroprosthetic Devices"; Science; bearing a date Jun. 7, 2002; pp. 1829-1832; vol. 296; www.sciencemag.org.

"Tiny Robot Reduces Need for Surgery"; Pink Tentacle; bearing a date of Feb. 26, 2007; p. 1; http://www.pinktentacle.com/2007/02/tiny-robot-reduces-need-for-surgery; printed on Mar. 8, 2007.

"Trying to control pain can be a double-edged sword, say scientists"; PhysOrg.com; printed on Nov. 2, 2006; pp. 1-2; http://www.physorg.com/printnews.php?newsid=81599312.

Tummala, R. Lal; Mukherjee, R.; Aslam, D.; Xi, Ning; Mahadevan, S.; Weng, J.; "Reconfigurable Adaptable Micro-robot"; IEEE; bearing a date of 1999; pp. 687-691.

Twardoch, U.M.; "Integrity of Ultramicro-Stimulation Electrodes Determined from Electrochemical Measurements"; Journal of Applied Electrochemistry; bearing a date of 1994; pp. 835-857; vol. 24; Chapman & Hall.

Warland, David K.; Reinagel, Pamela; Meister, Markus; "Decoding Visual Information from a Population of Retinal Ganglion Cells"; bearing a date of 1997; pp. 2336-2350; The American Physiological Society.

Weis, Rolf; Müller, Bernt; Fromherz, Peter; "Neuron Adhesion on a Silicon Chip Probed by an Array of Field-Effect Transitors"; Physical Review Letters; bearing a date of Jan. 8, 1996; pp. 327-330; vol. 76, No. 2; The American Physical Society.

Wessberg, Johan; Stambaugh, Christopher R.; Kralik, Jerald D.; Beck, Pamela D.; Laubach, Mark; Chapin, John K.; Kim, Jung; Biggs, S. James; Srinivasan, Mandayam A.; Nicolelis, Miguel A.L.; "Letters to Nature: Real-Time Prediction of Hand Trajectory by Ensembles of Cortical Neurons in Primates"; Nature; bearing a date of Nov. 16, 2000; pp. 361-365; vol. 408; Macmillan Magazines Ltd; www.nature.com.

White, Dave; "Mini Robot Explores, Gives you Medicine from Within"; Mobile Magazine; bearing a date of Feb. 27, 2007; p. 1; http://www.mobilemag.com/content/100/313/C118691; printed on Mar. 8, 2007.

Yusa, Go; Muraki, Koji; Takashina, Kei; Hashimoto, Katsushi; Hirayama, Yoshiro; "Controlled multiple quantum coherences of nuclear spins in a nanometre-scale device"; Nature; Apr. 21, 2005; pp. 1001-1005; vol. 434; 2005 Nature Publishing Group; www.nature.com./nature.

"Zyvex NanoEffector Microgrippers"; Nanotechnology at Zyvex; printed on Dec. 7, 2006; pp. 1-2; http://www.zyvex.com/Products/Grippers_Features.html.

"Zyvex NanoEffector Microgrippers"; Zyvex.com; bearing a date of 2006; pp. 1-2; Zyvex Corporation.

UK Intellectual Property Office Examination Report Under Section 18(3); App. No. GB0821519.6; Nov. 12, 2009; pp. 1-4.

UK Intellectual Property Office Examination Report Under Section 18(3); App. No. GB0821526.1; Nov. 11, 2009; pp. 1-5.

UK Examination Report Under Section 18(3); App. No. GB0821524.6; bearing a date of May 6, 2010 ; pp. 1-3.

UK Intellectual Property Examination Report Under Section 18(3); App. No. GB0706802.6; Nov. 23 2009; pp. 1-2.

UK Intellectual Property Office Examination Report Under Section 18(3); App. No. GB0821526.1; bearing a date of Jul. 15, 2010; received by our agent Jul. 16, 2010; pp. 1-2.

UK Intellectual Property Office Examination Report Under Section 18(3); App. No. GB0821524.6; Aug. 9, 2010 ; pp. 1-2.

UK Intellectual Property Office Examination Report Under Section 18(3); App. No. GB0821519.6; Aug. 9, 2010 ; pp. 1-3.

UK Intellectual Property Office Examination Report Under Section 18(3); App. No. GB0821530.3; Aug. 27, 2010 ; pp. 1-6.

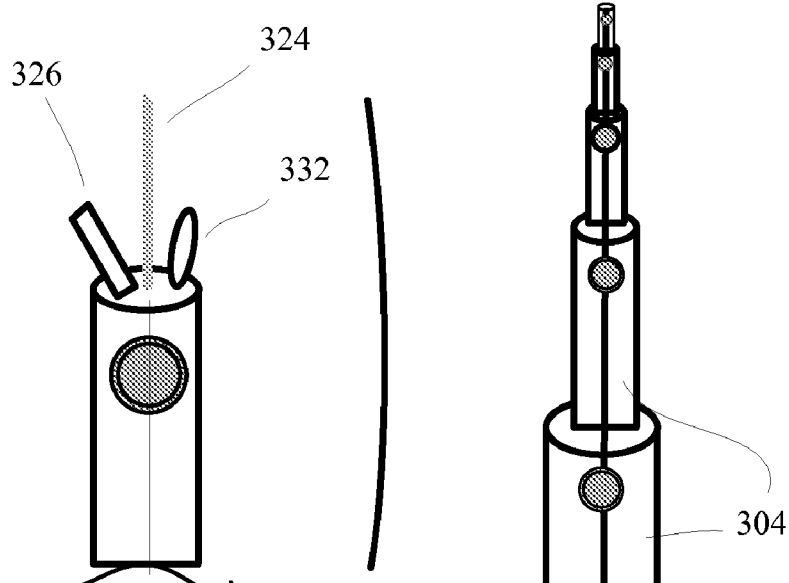
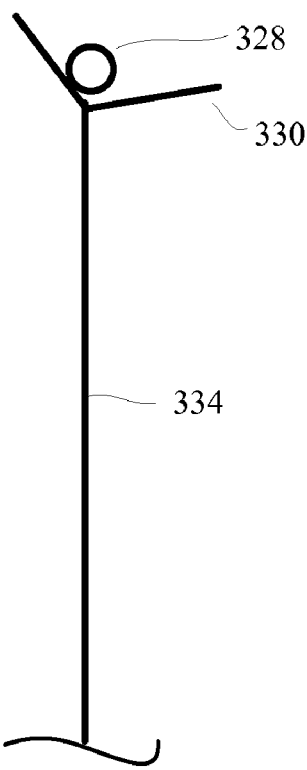
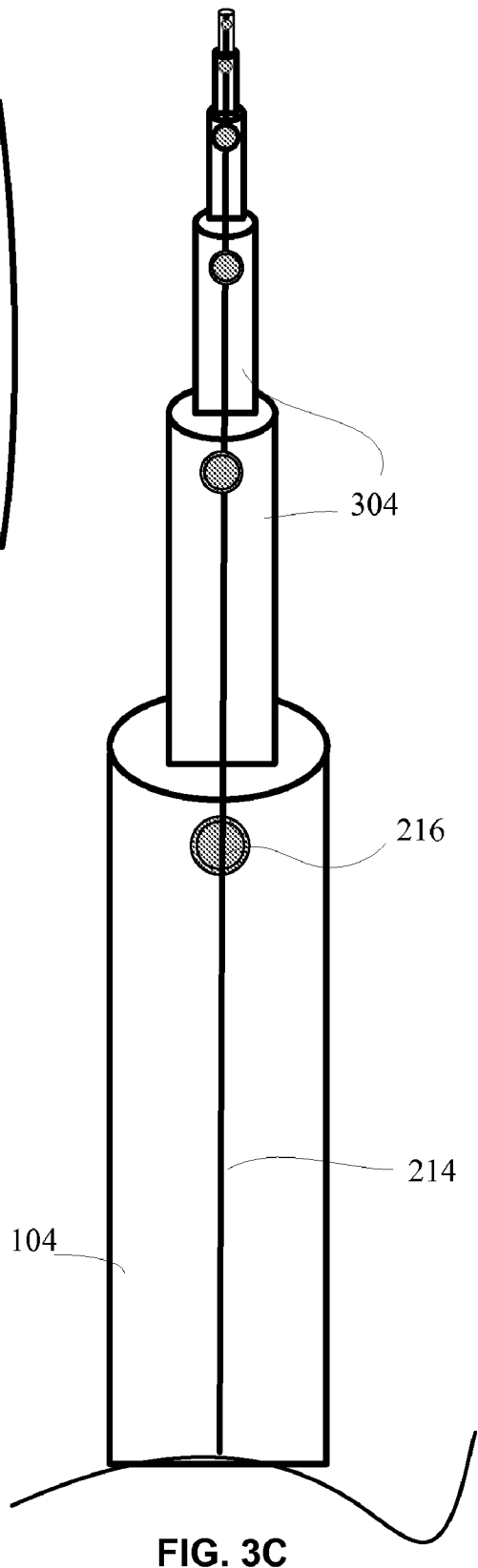
FIG. 3A
FIG. 3B
FIG. 3C

SYSTEM FOR PERFUSION MANAGEMENT

CROSS-REFERENCE TO RELATED APPLICATIONS

The present application is related to, claims the earliest available effective filing date(s) from (e.g., claims earliest available priority dates for other than provisional patent applications; claims benefits under 35 USC §119(e) for provisional patent applications), and incorporates by reference in its entirety all subject matter of the following listed applications; the present application also claims the earliest available effective filing date(s) from, and also incorporates by reference in its entirety all subject matter of any and all parent, grandparent, great -grandparent, etc. applications of the following listed applications:

1. U.S. patent application Ser. No 10/827,576 entitled A SYSTEM WITH A RESERVOIR FOR PERFUSION MANAGEMENT, naming Lowell L. Wood, Jr. as inventor, filed on Apr. 19, 2004.
2. U.S. patent application Ser. No. 10/827,578 entitled A SYSTEM WITH A SENSOR FOR PERFUSION MANAGEMENT, naming Lowell L. Wood, Jr. as inventor, filed on Apr. 19, 2004.
3. U.S. patent application Ser. No. 11/891,356 entitled A SYSTEM FOR PERFUSION MANAGEMENT, naming Lowell L. Wood Jr. as inventor, filed on Aug. 9, 2007.
4. U.S. patent application Ser. No. 11/891,333 entitled A SYSTEM WITH A RESERVOIR FOR PERFUSION MANAGEMENT, naming Lowell L. Wood Jr. as inventor, filed on Aug. 9, 2007.
5. U.S. patent application Ser. No. 11/891,355 entitled A SYSTEM WITH A RESERVOIR FOR PERFUSION MANAGEMENT, naming Lowell L. Wood Jr. as inventor, filed on Aug. 9, 2007.
6. U.S. patent application Ser. No. 11/891,573 entitled A TELESCOPING PERFUSION MANAGEMENT SYSTEM, naming Lowell L. Wood, Jr. as inventor, filed on Aug. 9, 2007.
7. U.S. patent application Ser. No. 11/891,371 entitled A TELESCOPING PERFUSION MANAGEMENT SYSTEM, naming Lowell L. Wood, Jr. as inventor, filed on Aug. 9, 2007.

TECHNICAL FIELD

The present application relates, in general, to detection and/or treatment.

SUMMARY

In one aspect, a system includes, but is not limited to at least one arm; a control circuit coupled to said at least one arm; at least one receptacle coupled to said at least one arm; and at least one sensor coupled to said at least one arm, said system configured for implantation in an animal. In addition to the foregoing, other system aspects are described in the claims, drawings, and text forming a part of the present application.

In one aspect, a method includes but is not limited to: making a device, by providing a cavity for storing a receivable; and including at least one transmitting channel coupled to said cavity for delivering said receivable from said cavity to a predetermined location in an animal, cooperative with a monitoring system and a detecting system including logic or software operative for delivering said receivable. In addition to the foregoing, other method aspects are described in the claims, drawings, and text forming a part of the present application.

In another aspect, a method includes but is not limited to: placing a device comprising a receiving unit for storing a deliverable and in communication with a pliable duct; directing said pliable duct to a location; and administering said deliverable from said receiving unit to said location cooperative with a guiding system and a detecting system. In addition to the foregoing, other method aspects are described in the claims, drawings, and text forming a part of the present application.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

In addition to the foregoing, various other method and or system aspects are set forth and described in the text (e.g., claims and/or detailed description) and/or drawings of the present application.

The foregoing is a summary and thus contains, by necessity; simplifications, generalizations and omissions of detail; consequently, those skilled in the art will appreciate that the summary is illustrative only and is NOT intended to be in any way limiting. Other aspects, inventive features, and advantages of the devices and/or processes described herein, as defined solely by the claims, will become apparent in the non-limiting detailed description set forth herein.

BRIEF DESCRIPTION OF THE FIGURES

FIGS. 3A, 3B, and 3C show exploded views of various aspects of the device of FIG. 1, including an extensible finger 104.

The use of the same symbols in different drawings typically indicates similar or identical items.

DETAILED DESCRIPTION

The present application uses formal outline headings for clarity of presentation. However, it is to be understood that the outline headings are for presentation purposes, and that different types of subject matter may be discussed throughout the application (e.g., device(s)/structure(s) may be described under the process(es)/operations heading(s) and/or process(es)/operations may be discussed under structure(s)/process(es) headings). Hence, the use of the formal outline headings is not intended to be in any way limiting.

1. Perfusion Management Device(s) and/or Process(es)

Figure 1:
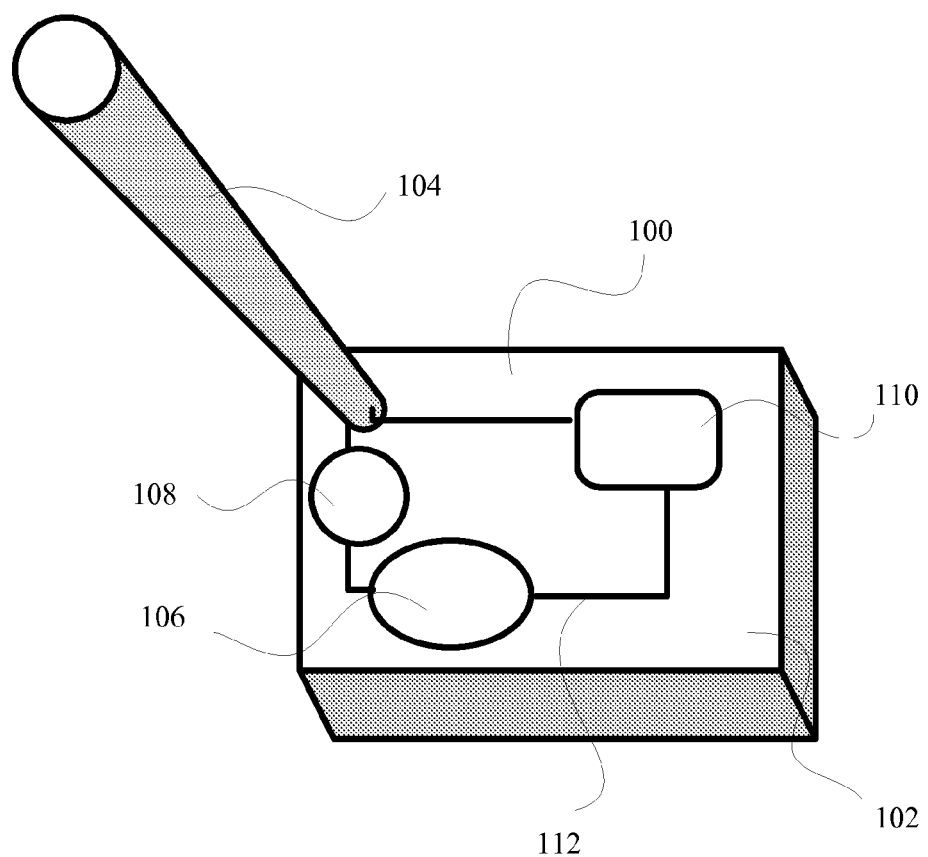
FIG. 1 is a front-plan view of a device for perfusion management 100.

With reference now to FIG. 1, shown is a front plan view illustrative of various exemplary perfusion management device(s) and/or process(es). Accordingly, the present application first describes certain specific exemplary structures of FIG. 1; thereafter, the present application illustrates certain specific exemplary processes. Those having skill in the art will appreciate that the specific devices and processes described herein are intended as merely illustrative of their more general counterparts.

A. Structure(s) and or Device(s)

With reference to the figures, and with reference now to FIG. 1, shown is a front-plan view of a device for perfusion management 100. The device for perfusion management 100 includes a body portion 102 from which at least one arm 104 projects. A receptacle 106 within the body portion 102 contains a fluid, for example, a fluid for treatment. A controllable valve 108 provides a path through which the fluid may travel to the at least one arm 104.

A control circuit 110 provides a control signal that may open or close the control valve 108. The control circuit 110 may be connected to a sense line 112 that allows it to monitor the fluid levels within the receptacle 106. Additionally, a sense line 114 connects the control circuit 110 to a sensor 116 at the distal end of the at least one arm 104.

Figure 2:
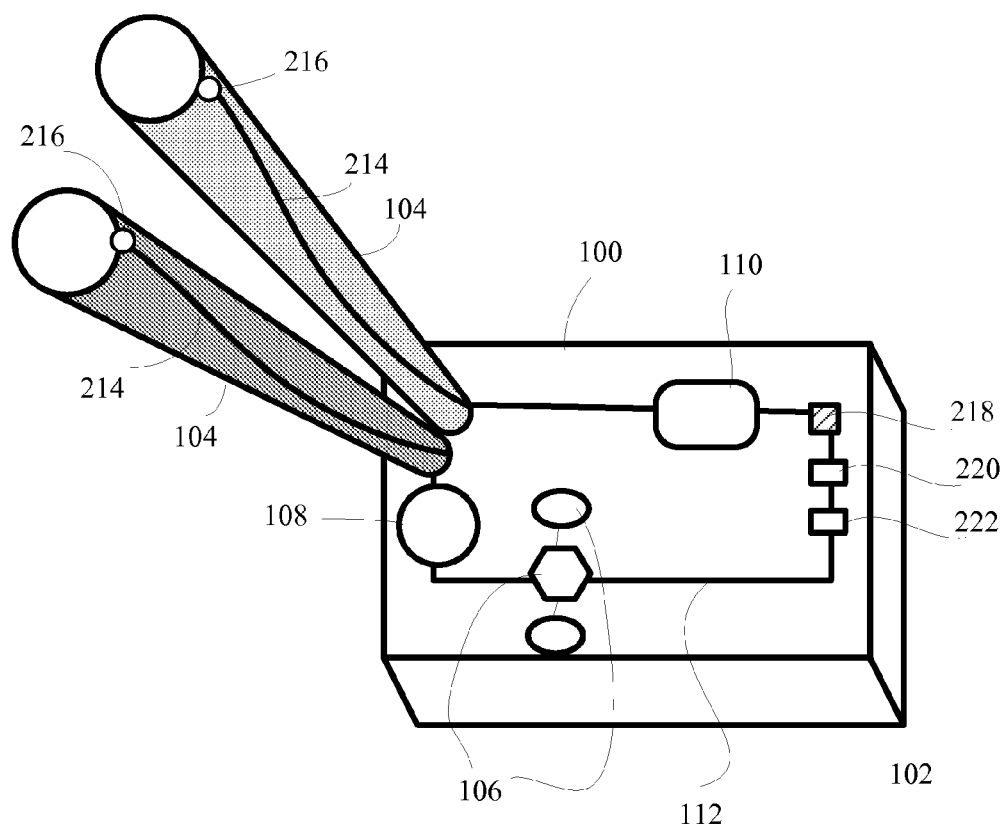
FIG. 2 is a front-plan view of another aspect of the device for perfusion management 100.

Referring now to FIG. 2, depicted is an aspect of the device for perfusion management 100 which includes the body portion 102 from which a set of at least one arm 104 projects. In one aspect, each of the at least one arm 104 is in fluid communication with a respective receptacle 106. Each receptacle 106 may be filled with a different fluid for delivery. In another approach, the one or more receptacles 106 may be coupled to a mixing chamber 224 where the fluid contents of each receptacle 106 are present for mixing and the mixed contents enter the arm for delivery to a selected location. The choice of fluid in the receptacle 106 may depend, for example, on the purpose of the device, for example, treatment of colon cancer, treatment of breast cancer, or treatment of an arterial disease. The choice of fluid in the receptacle 106 includes, but is not limited to, for example, a chemical, a chemical compound, a protein, a lipoprotein, a glycoprotein, a sugar, a lipid, an antigen, an antibody, a cytokine, a peptide, a neurotransmitter, a hormone, an ion, a messenger a molecule, a nucleic acid, an engineered nucleic acid, a nucleic acid vector, a drug, a cell, a cell fragment, a cell organelle, a liposome, a pharmaceutical agent, a biological material, or a biological fraction. The receptacle 106 may also be utilized for storage and disposal of operational fluids. Also, although the exemplary embodiment described herein focuses primarily on fluid delivery, one skilled in the art will understand that fluid-like substances, such as gels, and fluidizable substances or non-fluid type substances, such as small solid particles, may be delivered in accordance with the invention. It will also be appreciated by those having skill in the art that the nature of the fluid in the receptacle 106 includes, for example, and is not limited to, a liquid, a solution, a mixture, a gel, a colloid, a colloid of a suitable viscosity, a suspension, an emulsion, or any material of low shear-strength for delivery to a site.

In one aspect one or more fluids are delivered to one or more of selected locations by the device for perfusion management 100. The selected location may be, for example, in proximity to or within a tumor, a circulatory system, an aorta, a vena cava, a site of therapy, or a site of investigation in an animal.

Continuing to refer to FIG. 2, a pump 218 provides fluid at a controlled flow rate for delivery to a site from the receptacle 106. It will be appreciated by those skilled in the art that the type of pump is not critical to the invention and may include, for example, a mechanical pump, a piezoelectric pump, an osmotic pump, a source of pressure, or a device for maintaining a positive flow of fluid through the device. Additionally, fluid flow may be further modulated with micro valves and self-pressurizing fluidic reservoirs. Moreover, in some applications, the fluid may be delivered without a pump. For example, fluid delivery may be controlled using a pressurized bladder, controlled dissolution or dilution of a material, a drip or gravity type of approach, or any other suitable approach to deliver an appropriate amount or an appropriate delivery-rate of the fluid.

With reference now to FIG. 3, depicted is an exploded view of the arm 104 showing a plurality of extended parts 304 with the sensor 116 at the distal end of each of the extended parts 304. In one aspect of the invention, the sensor 116 is an array of sensors, deployed from one or more portholes, at the distal end of each of the extended parts 304. In one approach, the portholes are sized and shaped to provide access through which the sensors 116 may be deployed. The portholes may include seals, stress relief or other features appropriate for proper mechanical deployment. In one approach, one or more of the portholes can be controllably opened or closed to provide communication exterior to the arm or main body. The sensor 116 may be retracted within the porthole and deployed through the porthole. Where the porthole can be opened and closed, the porthole can close to limit communication and can be opened for deployment. The array of sensors may include, but is not limited to, for example, sensors for detecting pressure, temperature, chemical, gas, electrolyte, flow, volume, composition, or concentration. In an alternate aspect of the invention, microelectrodes, such as, for example, solid-state microlectrodes, are sensitized with an agent for detecting a relevant interacter. Examples of the agent include, but are not limited to, for example, agonists of angiogenesis. The choice of sensor 116 depends on the physiological variable being monitored, treated, or controlled. The term "physiological variable" refers to any and all measurements relating to the functioning of a living organism in normal, sub-normal, or abnormal states.

Figure 4:
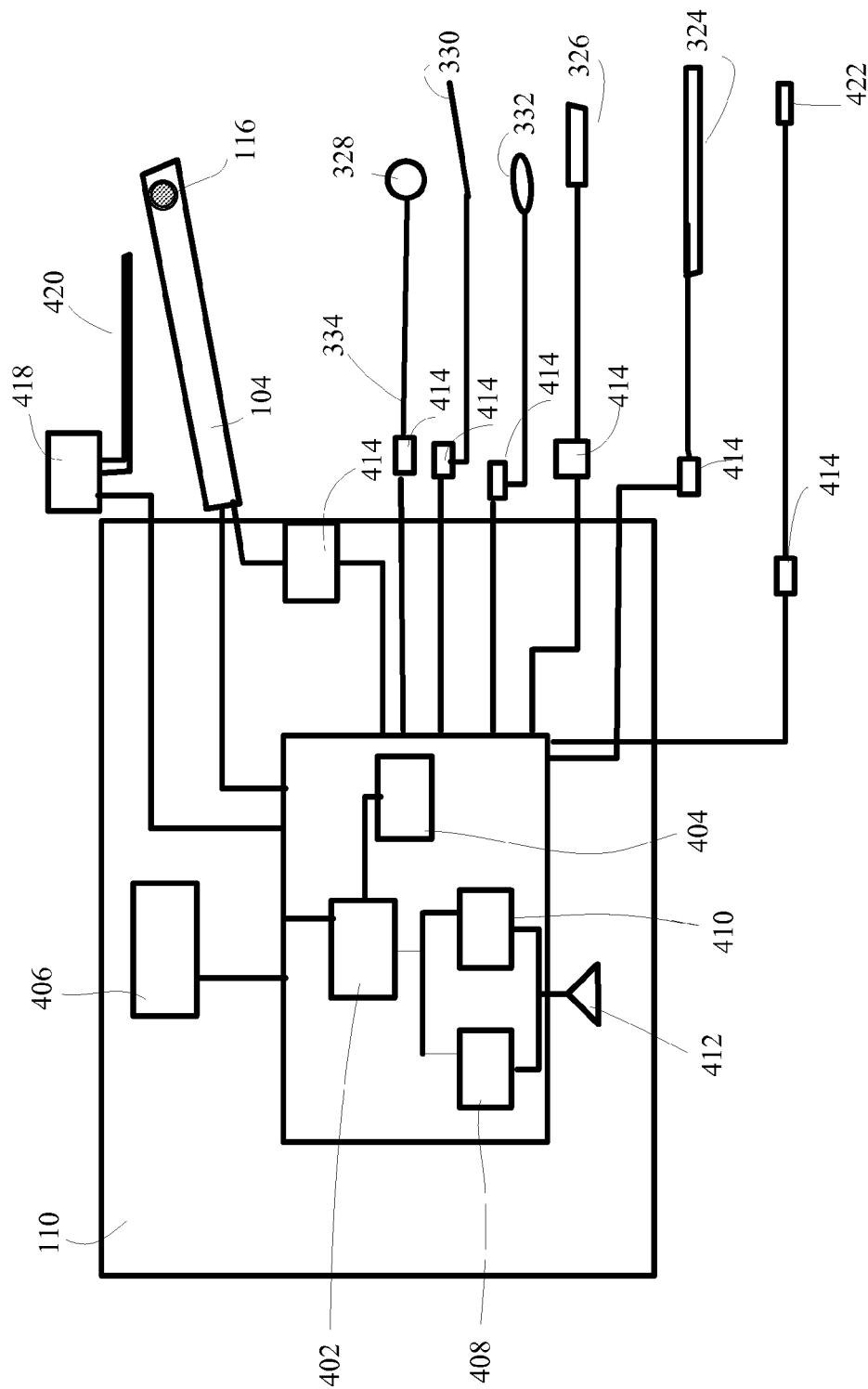
FIG. 4 is a schematic view of the control circuit 110 and devices in communication with the control circuit 110.

Continuing to refer to FIG. 3 and referring now to FIG. 4, an operative tool 324 is coupled to the distal most extended part 304, or deployed from the porthole, or carried by the arm 104, further including a carrying line 334 in communication with the control circuit 110. The operative tool 324 includes, but is not limited to, for example, one or more of a combination of, a tool positioner, an ablation device, a laser, a vacuum, a siphon 326, an evacuation device, a fluid dispenser 328, a cauterizer 330, a stent 332, a tissue-liquefying device, or a source of an electric charge or electromagnetic radiation 422. The vacuum or the siphon 326 is employed for removing a cell, a mass of cells, a tissue, a fluid, a gel, a sample, a debris, a contaminant, or other material for which removal is desired or appropriate. The ablation device operates for perturbing or reducing the structural integrity or viability of a cell, a mass of cells, an assembly of biological materials exhibiting shear strength, or a tissue. The assembly of biological materials includes, for example, blood clots, cartilage, or bone. The source of an electric charge or electromagnetic radiation 422 includes, but is not limited to, for example, steady state electric currents, time-varying electric currents, alternating electric currents, radio waves, microwaves, ultraviolet rays, infrared rays, optical rays, terahertz beams, and the like.

Continuing to refer to FIG. 3, it will be appreciated by those having skill in the art that the operative tool 324 may include a set of devices having general or "multi-purpose" utility. The operative tool 324 may include, but is not limited to, for example, a combination of the fluid dispenser 328, the siphon 326, and the ablation device. In this example the operative tool combination, for example, delivers the fluid or gel, ablates cells, and removes debris.

Continuing to refer to FIG. 3, the plurality of extended parts 304 may themselves be hollow forming a conduit for delivery of the fluid to a site, or for housing a circuitry coupling the control circuit 110 to the operative tool 324, or for housing a mechanism that guides the arm 104 or the plurality of extended parts 304.

With reference now to FIG. 4, illustrated is a schematic view of the control circuit 110 and devices in communication with the control circuit 110. The device for perfusion management 100 shows a data transmitter 410, and a data receiver 408 coupled to the control circuit 110. An antenna 412 may be used for transmitting data to the exterior wirelessly. The antenna 412 is shown diagrammatically, but may be a structure, such as a strip antenna, that may be integrated in a manner that does not impair or significantly perturb system performance. The control circuit 110 is depicted as having a processor 402 coupled to a memory 404 that provides data storage and retrieval capability, and a power source 406. Feedback circuitry or logic circuitry provides communication between the control circuit 110 and devices in communication with it. In some applications, a software program providing instructions may be stored in the memory 404 to control operation of the control circuitry or to store data gathered under control of the control circuitry. Additionally, the control circuit 110 may have components for system integrated digital data gathering, processing, storage, compression and transmission. These can provide data control capabilities and operation control capabilities. For example, the transmission components may communicate through the antenna 412 to a person, system, computer, or device exterior to the body. This communication can allow data gathered by the sensors to be displayed, stored or otherwise processed in the external environment. Additionally, this communication may allow for the processed data or a plurality of new data to be received from the exterior by the device for perfusion management 100. Data compression can allow the control circuitry to store data representing larger amounts of data to be stored in the memory 404 or to be transmitted to the exterior environment in a more efficient manner.

Continuing to refer to FIG. 4, one or more of the operative tools 324 are mounted on an actuator 414 which allows for the independent movement of each tool. Alternatively, one or more operative tools 324 may be mounted as a unit on one actuator 414 and moved as a group, for example, forming an aspirating-dispensing unit. For example, the fluid dispenser 328 and the siphon 326 may be mounted together as a group. The actuator 414 may be a motor, a piezo electrically driven actuator, a micromechanical or electrical effector, or the like.

Continuing to refer to FIG. 4, the arm 104 may include an imaging device deployed from the porthole or from the distal end of the arm 104 or carried by a carrying line 334. The term "imaging device" being used herein to designate in general those components, circuits, assemblies and sub-assemblies comprising electrical, optical, acoustic, or opto-electronic components. In one aspect, the control circuit 110 is coupled to the imaging device that includes a laser 418, or a source of light or scene-illuminating radiation, coupled to an optical feed line 420 to illuminate an area. A charge coupled device is positioned to capture data from the illuminated area and provides an electronic signal indicative of the area imaged. Conventional circuitry then produces a digital representation that may be displayed, stored in the memory 404, or otherwise processed. The displayed image may serve, for example, for guiding the arm 104 to the selected location or for determining the efficacy of a treatment or a procedure. One skilled in the art will recognize that the imaging device described herein is exemplary of imaging devices and that other imaging devices, including for example, raster and line-scanning imagers, nonvisible spectral imagers, and fluorescence imagers, may be included.

Figure 5:
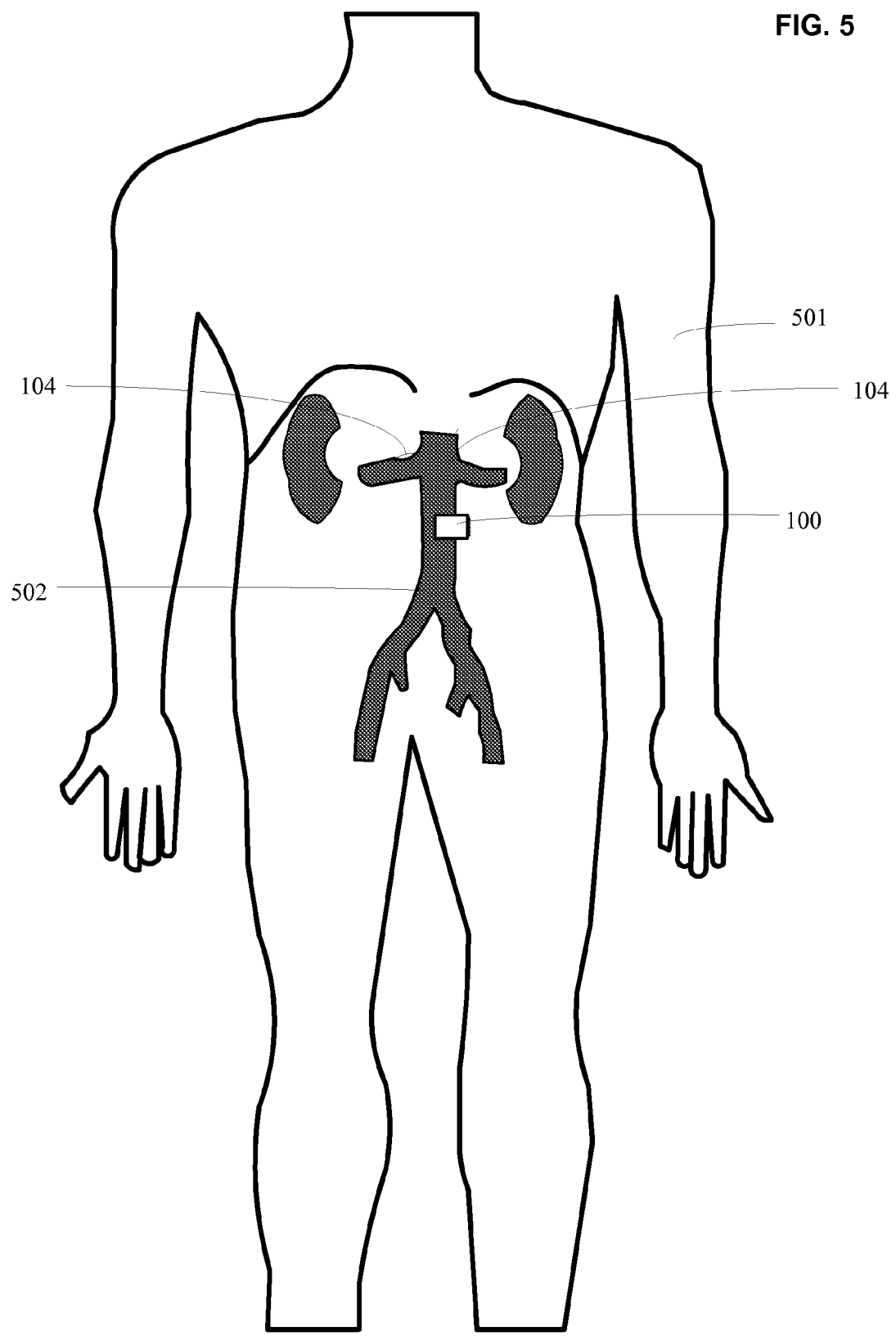
FIG. 5 illustrates an example wherein the device for perfusion management 100 is placed in a selected location in a human body 501.

With reference now to FIG. 5, the device for perfusion management 100 is depicted implanted in an aorta 502 with the arm 104 traveling a blood vessel in a human body 501. Additionally, the device for perfusion management 100 is configured for full or partial placement in the human body 501. The configuration may incorporate a combination of the following criteria, including but not limited to, dimensions, composition, shape, power dissipation level, or texture. In one aspect, the body portion 102 is sized for implantation in proximity to the aorta 502 or the vena cava and the arm 104 is sized for traveling a blood vessel in an animal, for example, the human body 501. In this aspect, if the vasculature decreases two-fold, each of the extending parts 304 has about a two-fold decrease in diameter. The length of the arm 104, for example, depends upon the distance between the selected location and the location of the body portion 102, and the route traveled by the arm 104 to arrive at the selected location. It will be appreciated by those having skill in the art that the arm 104 including the one or more of the operative tools 324 is of a size, dimension or shape operable for traveling one or more blood vessel of decreasing or increasing luminal diameter. It will also be appreciated by those having skill in the art that the arm 104 and the one or more operative tool 324 may pass through the wall of a lumen, or trans-luminally, to the surrounding tissue for detecting, delivery of a treatment, or for sampling. It will also be appreciated by those having skill in the art that the trans-luminal mode described is not limited to blood vessels and includes the space or cavity of an organ or structure.

It will also be appreciated by those having skill in the art that the device for perfusion management 100 and its components, such as, for example, the arm 104, the plurality of extended parts 304, or one or more operative tools 324, has a size, dimension, shape, material, and properties of flexion, retraction, and extension to allow for the steering, guiding, or positioning of the components of the device for perfusion management 100. For example, the arm 104 may need to be steered around an occlusion or a fork in the vasculature. In this example, the arm 104 may need to retracted, repositioned and then extended in a new direction. Extending, retracting or repositioning of the arm 104 may be accomplished by techniques known in the art, for example, by using a guide wire or a by employing a shape polymer. In another aspect, the arm may be retracted and then "punched through" an occlusion to dislodge, penetrate, or grapple it. In this example, a laser beam, a shearing tool, a cutting tool, or a drug, for example, a lytic drug, may be employed to degrade or reduce the occlusion. In this example, subsequent to the dislodgement and degradation of the occlusion, the siphon 326 or an evacuation device is employed to evacuate any debris, before the arm 104 continues traveling the circulatory system. It will also be appreciated by those skilled in the art that the device for perfusion management 100 is not restricted to traveling the circulatory system but may be implanted in any tissue, such as, for example, nerve, epithelial, dermal, sub-dermal, connective, or muscle tissue. Additionally, the device for perfusion management 100 may be implanted in inter-tissue spaces, or inter-organ spaces, for example, those found within a body cavity.

In one aspect the device for perfusion management 100 includes an array of sensors 116 positioned across the plurality of extended parts 304 for monitoring, tracking, or mapping a gradient of temperature, pressure, flow, or material concentration in one or more locations. The one or more locations may be, for example, a tissue, an artery, or a vein. In another aspect the device for perfusion management 100 has an auto-correct feature for correcting a sub-normal or abnormal gradient of temperature, pressure, flow, or material concentration. In yet another aspect the device for perfusion management 100 has an auto-correct feature for detecting and correcting a sub-normal or abnormal gradient of temperature, pressure, flow, or material concentration.

The device for perfusion management 100 may be composed of materials known in the art, for example, a metal, a ceramic, a glass, a plastic, a polymer, a biologically compatible material, or a combination. For example, the device for perfusion management 100 may be made of helically-coiled stainless steel wire and coated with a polymer, such as, Teflon™. In another example; the device for perfusion management 100 may be made of helically-coiled stainless steel wire and coated with a polymer and impregnated with one or more of a biological material, for example, including but not limited to, anti coagulants, or inhibitors.

B. Operation(s) and/or Process(es)

Those having skill in the art will appreciate that some or all of the components of the device for perfusion management 100 may be present ex vivo. In one implementation, the device for perfusion management 100 is placed in proximity to the location on the animal, for example, the human body 501, and the at least one arm 104 directed to the selected location and an effective agent delivered in proximity to the selected location. The arm 104 may be retracted after such a delivery, leaving the device for perfusion management 100 in place at the location, until time for a future delivery of the effective agent or another procedure or operation. In this implementation, the majority of the device for perfusion management 100 is ex vivo while the arm 104 alternates between ex vivo and in vivo states.

In another aspect, some or all the components of the device for perfusion management 100 are present in vivo. In one implementation, the device for perfusion management 100 is placed in proximity to the location within the animal, for example, the human body 501, and the arm 104 directed to a selected location and an effective agent delivered in proximity to the selected location. The arm 104 may be retracted after such a delivery, leaving the device for perfusion management 100 in place at the location, until time for a future delivery or another operation. In this implementation, the majority of the device for perfusion management 100 is in vivo while the arm 104 alternates between retracted, partially retracted or unretracted states.

In one implementation, the device for perfusion management 100 is operable by a person. The person monitors, guides, positions, and performs other actions/operations or manages a response consistent with the device for perfusion management 100 being managed by the person. In such an implementation a separate display device can present imagery to aid the person. The imagery may be captured as described above with reference to FIG. 4, may be computer generated or may be captured by a separate imaging device internal to or external to the animal, for example, the human body 501. Actions may be performed under control of the person who may be on site or may be linked from a remote location, or the device for perfusion management 100 may be programmed to perform some or all functions automatically. For example, the device for perfusion management 100 may be programmed to perform functions, such as, lumen clearance, lumen maintenance, monitoring of concentrations, sending of alerts, delivery of one or more of the effective agent at timed intervals or locations, self-check, or self-diagnosis. It will be appreciated by those of skill in the art that the device for perfusion management 100 may be programmed for complete automatic operation of one or more functions.

C. Variation(s), and/or Implementation(s)

Those having skill in the art will recognize that the present application teaches modifications of the devices, structures, and/or processes within the spirit of the teaching herein. For example, the device for perfusion management 100 need not be limited to managing perfusion. The device provides a mechanism for exploring one or more regions and/or reaching a location within an animal, obtaining information, communicating this information, performing operations, performing procedures, or providing treatment. The treatment includes but is not limited to, for example, treatment of a subnormal, abnormal or pathological condition. In another example, the device for perfusion management 100 may find utility in the management of physiological functions, the detection or elimination of pathological functions or conditions, and/or treatment of a disease or a pathological state of non-human animals. Other modifications of the subject matter herein will be appreciated by one of skill in the art in light of the teachings herein.

The foregoing described aspects depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality.

While particular aspects of the present subject matter described herein have been shown and described, it will be obvious to those skilled in the art that, based upon the teachings herein, changes and modifications may be made without departing from this subject matter described herein and its broader aspects and, therefore, the appended claims are to encompass within their scope all such changes and modifications as are within the true spirit and scope of this subject matter described herein. Furthermore, it is to be understood that the invention is defined solely by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations), etc.

Furthermore, in those instances where a convention analogous to "at least one of A, B, and C, etc." is used, in general such a construction is intended in the sense one having skill in the art would understand the convention (e.g., " a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., " a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A method for making a device, comprising:
   providing a cavity for storing a receivable;
   including at least one transmitting channel coupled to said cavity for delivering said receivable from said cavity to a predetermined location in an animal, cooperative with a monitoring system and a detecting system including logic and/or software operative for delivering said receivable; and
   coupling one or more operative tools deployable via one or more openable and/or closeable portholes to the transmitting channel.

2. The method according to claim 1, further comprising transferring a fluid to said cavity.

3. The method according to claim 2, wherein said device includes a pump, and/or a source of pressure, coupled to said cavity for transferring said fluid.

4. The method according to claim 1, further comprising coupling a motor and/or an actuator to said at least one transmitting channel.

5. The method according to claim 1, further comprising configuring said device to be monitored and/or controlled by a person.

6. The method according to claim 1, further comprising configuring said device for implantation in said predetermined location in said animal.

7. The method according to claim 1, further comprising coupling said cavity to a mixing cavity.

8. The method according to claim 1, further comprising coupling a source of a chemical, a chemical compound, a protein, a lipoprotein, a glycoprotein, a sugar, a lipid, an antigen, an antibody, a cytokine, a peptide, a neurotransmitter, a hormone, an ion, a messenger molecule, a nucleic acid, an engineered nucleic acid, a nucleic acid vector, a drug, a cell, a cell fragment, a cell organelle, a liposome, a pharmaceutical agent, a biological material, and/or a biological fraction internal and/or external to said cavity.

9. The method according to claim 1, further comprising coupling a source of two or more of a chemical, a chemical compound, a protein, a lipoprotein, a glycoprotein, a sugar, a lipid, an antigen, an antibody, a cytokine, a peptide, a neurotransmitter, a hormone, an ion, a messenger molecule, a nucleic acid, an engineered nucleic acid, a nucleic acid vector, a drug, a cell, a cell fragment, a cell organelle, a liposome, a pharmaceutical agent, a biological material, and/or a biological fraction internal and/or external to said cavity.

10. The method according to claim 1, further comprising coupling a device for data gathering, processing, storage and/or transmission to said monitoring system and/or said detecting system.

11. The method according to claim 1, wherein said monitoring system communicates wirelessly.

12. The method according to claim 1, wherein said monitoring system is operative for guiding and/or extending and/or moving said transmitting channel.

13. The method according to claim 1, wherein said monitoring system comprises a processor, a feedback circuit, and/or a logic circuit.

14. The method according to claim 1, wherein said monitoring system is a processor further comprising a stored software and/or firmware program cooperative with said processor.

15. The method according to claim 1, wherein said transmitting channel is formed from a plurality of extending parts.

16. The method according to claim 1, wherein said plurality of extending parts includes portions that are hollow.

17. The method according to claim 1, further comprising coupling a flow regulator and/or a flow monitor to said transmitting channel and/or said cavity.

18. The method according to claim 1, further comprising coupling a device for partially blocking and/or shunting a liquid flow to said transmitting channel.

19. The method according to claim 1, further comprising coupling a dispenser to said transmitting channel, said dispenser including a fluid controller operative to provide a fluid at a controlled rate.

20. The method according to claim 1, further comprising coating said at least one transmitting channel with a polymer and/or a biocompatible material.

21. The method according to claim 1, wherein said detecting system includes coupling an imager, a pressure sensor, a temperature sensor, a chemical sensor, a gas sensor, an electrolyte sensor, a concentration sensor, a composition sensor, and/or a flow sensor coupled to said at least one transmitting channel.

* * * * *